United States Patent [19]

Shukla et al.

[11] Patent Number: 5,625,344
[45] Date of Patent: Apr. 29, 1997

[54] LOW FLUID LEVEL WARNING DEVICE

[76] Inventors: Ashok K. Shukla; Mukta Shukla, both of 10024 Century Dr., Ellicott City, Md. 21042

[21] Appl. No.: 201,793

[22] Filed: Feb. 25, 1994

[51] Int. Cl.⁶ .................................................. G08B 21/00
[52] U.S. Cl. .......................... 340/623; 340/603; 340/618; 340/624; 200/61.45 R; 200/84 R; 200/220; 200/223; 200/230
[58] Field of Search ........................ 340/603, 618, 340/623, 624; 200/61.45 R, 61.52, 84 R, 84 C, 220, 230, 223

[56] References Cited

U.S. PATENT DOCUMENTS

| | | | |
|---|---|---|---|
| 2,692,652 | 10/1954 | Wilson | 200/220 X |
| 3,211,853 | 10/1965 | Le Corvoisier | 200/84 R |
| 4,399,338 | 8/1983 | Jones | 340/625 X |
| 4,912,662 | 3/1990 | Butler et al. | |
| 4,922,234 | 5/1990 | Murphy | 200/84 R X |
| 5,228,304 | 7/1993 | Ryan | 340/623 X |

*Primary Examiner*—John K. Peng
*Assistant Examiner*—Edward Lefkowitz

[57] ABSTRACT

A device for warning when a low fluid level is reached is provided in which a levelness detecting switch is encapsulated in a conically shaped inert material (such as TEFLON™), sized appropriately to the predetermined fluid limit, and coupled to an alarm device (such as an audible alarm, a frequency signal or a light).

8 Claims, 4 Drawing Sheets

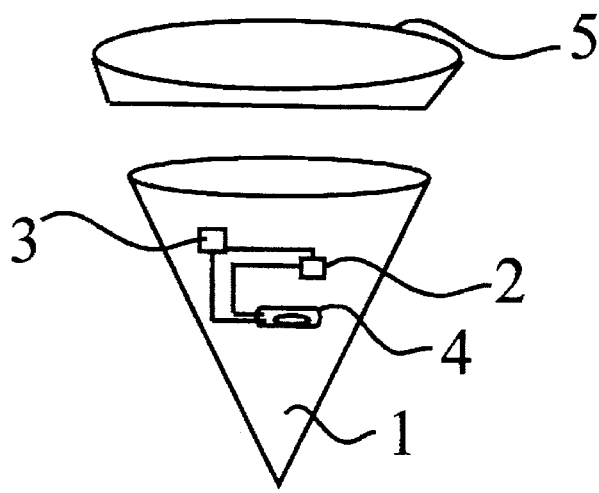 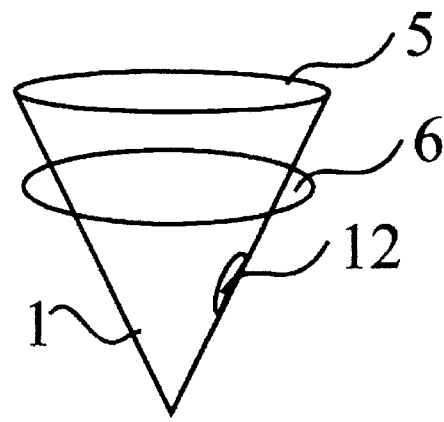
FIG. 1  FIG. 2
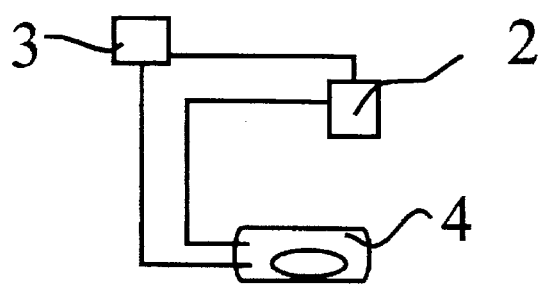 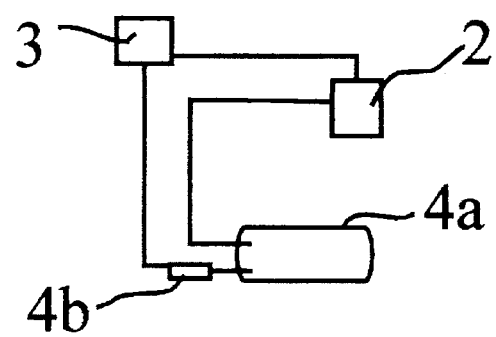
FIG. 3  FIG. 4

LOW FLUID LEVEL WARNING DEVICE

BACKGROUND OF THE INVENTION

The present invention relates in general to devices which warn when a fluid level drops below a predetermined limit, and in particular to a new and useful device which uses a separate levelness sensor to trigger an alarm when the fluid level in a container drops below a predetermined limit. A novel type of mercury switch, useful in connection with the invention is disclosed.

The invention described and claimed herein comprises a levelness sensor (for example, a mercury switch) encapsulated in a conically shaped inert material (such as TEFLON™), sized appropriately to the predetermined fluid limit, and coupled to an alarm device (such as an audible alarm, a radio frequency signal or a light emitting diode).

There are many situations in which undesirable results will follow if a given fluid level drops below some critical point. For example, in column chromatography, a solvent flows through a column and various chemicals and biochemicals are separated. The solvent is applied to the column by means of a pump or hydrostatic pressure to maintain a steady solvent flow through the system. If the containers with the solvent run empty then the column runs dry, which can destroy the column and the separation process. In the home, if a container of liquid is left on a stove to boil and boils dry, the container may be destroyed and may cause a fire. More generally, the status (empty or not) of an opaque container, for example a coffee carafe, can be determined, and can even be monitored remotely.

Inclinometers are well-known in the art. See, for example, U.S. Pat. No. 4,912,662 (INCLINOMETER) issued Mar. 27, 1990 to Butler et al., which is incorporated herein by reference. The special aspect of a mercury switch, that it is triggered by the flow of liquid mercury which by nature will remain level, has previously been used as a levelness sensing device in the broad sense. U. S. Pat. No. 2,692,652 (SAFETY DEVICE FOR USE WITH TRACTORS AND THE LIKE) issued Oct. 26, 1954 to Wilson couples such a switch to the power system of a tractor so as to stop the engine when a tractor travelling over uneven ground tilts to an unsafe level. The Wilson patent describes the operation of a mercury switch, and is incorporated herein by reference. The invention disclosed herein, however, couples the inherent level-sensing property of the mercury switch with a shape deliberately designed to tilt out of level when the fluid in which it floats no longer supports it.

Among the objects of the present invention are to provide a new and useful apparatus which warns when a fluid level drops below a predetermined limit and which has the additional advantages of being able to transmit the alarm to a remote location; of using very little energy except when in an alarm mode and thereby being suitable for encapsulation with a power source such as a lithium battery and thus requiring no external power cables; of being capable of manufacture in a small package suitable for use in small containers; of being self-contained and therefore washable and autoclaveable; of being suitable for manufacture of an inert material and therefore being suited to use in sterile or corrosive environments; and of being able to accommodate additional sensor and signalling devices in the same package.

These and other objects, advantages and features of the invention which will be apparent from the discussion which follows are achieved, in accordance with the invention, by providing a levelness sensor (for example, a mercury switch) encapsulated in a conically shaped inert material (such as TEFLON™), sized appropriately to the predetermined fluid limit, and coupled to an alarm device (such as an audible alarm, a radio frequency signal or a light emitting diode). While any levelness sensor may be used, the description which follows will use the example of a mercury switch as the levelness sensor.

The various features of novelty which characterize the invention are pointed out with particularity in the claims annexed to and forming a part of this disclosure. For a better understanding of the invention, its advantages and objects, reference is made to the accompanying drawings and descriptive matter in which a preferred embodiment of the invention is illustrated.

BRIEF DESCRIPTION OF THE DRAWINGS

The foregoing and still other objects of this invention will become apparent, along with various advantages and features of novelty residing in the present embodiments, from study of the following drawings, in which:

FIG. 1 is an expanded view of one embodiment of a device according to the present invention.

FIG. 2 is a side view of the device with a weight ring for changing the weight for particular fluid density.

FIG. 3 is an enlarged view of a portion of FIG. 1, comprising the schematic of a sample circuit diagram which could be embodied in the device.

FIG. 4 is an alternative circuit which could be embodied in a device using an inclinometer.

DESCRIPTION OF THE PREFERRED EMBODIMENT

Figure 5A:
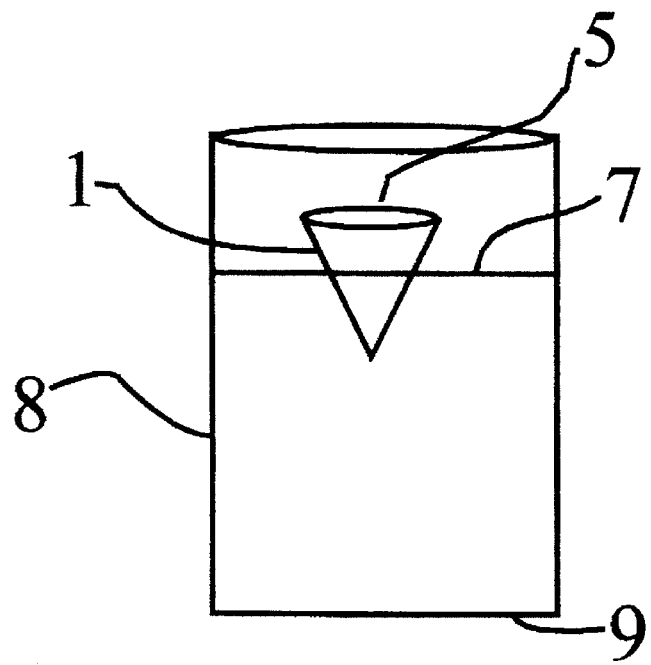
FIGS. 5a and 5b are a side view of the device in a container of fluid, illustrating the device in a ready mode (FIG. 5a) and in an alarm mode (FIG. 5b).

Referring to the drawings, the invention is a levelness sensor (for example, a mercury switch) encapsulated in a conically shaped inert material (such as TEFLON™) (1), sized appropriately to the predetermined fluid limit, and coupled to an alarm device (2) (such as an audible alarm, a radio frequency signal or a light emitting diode), powered by a battery (3) in series with a mercury switch (4) and sealed by a cap (5) shown in overview in FIG. 1.

Referring to FIG. 1, the invention is embodied in a conical shape device (1), which may be hollow, but must be of a density that can float on the liquid surface, as shown schematically in FIG. 1. As shown in FIG. 2 a weight ring (6) is provided if necessary to suit the density of the fluid for which it is to be used. The device (1) can be made of TEFLON™ or any inert material which does not react with the fluid in the container. The device (1) is sealed by cap (5), which can be permanently sealed if desired, or which may be resealable to allow for changing the mercury switch (4), the alarm device (2), circuitry or the battery (3) or for adding other elements. Alternative circuits are shown in FIGS. 3 and 4 where in FIG. 4 an inclinometer (4a) coupled to a switch (4b) replaces the mercury switch of FIG. 3.

The alarm could be a light source (for example, a light emitting diode), sound (beeper), or a transmitter (for example, a frequency generator).

The shape of the device (1) can be other than conical, but the geometry should be such that it floats stably in the fluid to avoid unintentionally activating the mercury switch. The device should be of such a size and density that it will float until the desired low level of fluid is reached, and then will contact the bottom of the container, tilt, and activate the mercury switch.

A conventional mercury switch measures levelness in one direction only. If such a Switch is used, it is necessary to assure that the device will tip in the direction necessary to close the switch. As illustrated in FIG. 2, this may be accomplished by adding a small weight (12) to the device in the direction of desired tilt. The mercury switch is then mounted in the device so as to be level in operation, accounting for the tilt imparted by the extra weight.

Figure 7:
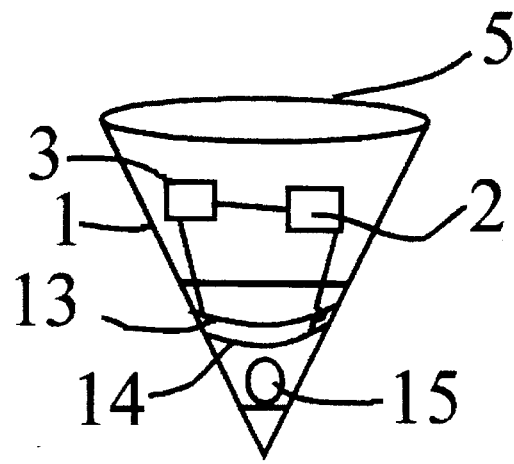
FIG. 7 is a side view of the device incorporating two conducting rings along the wall of the cone.

Alternatively, a conical mercury switch could be used. As illustrated in FIG. 7, such a conical switch could be constructed with two conducting rings (13 and 14) along the wall of the cone (1). The conducting rings (13 and 14) are attached to different leads so that when the device tilts a predetermined amount no matter to which side it tilts the mercury (15) will create a contact between the two rings.

Figure 5B:
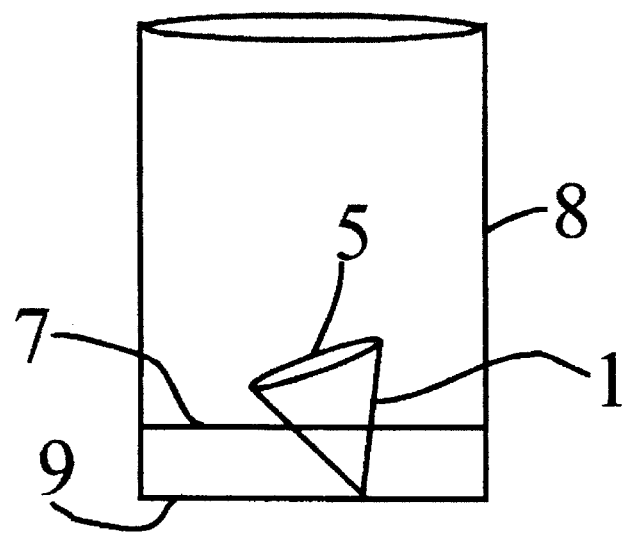
Figure 6A:
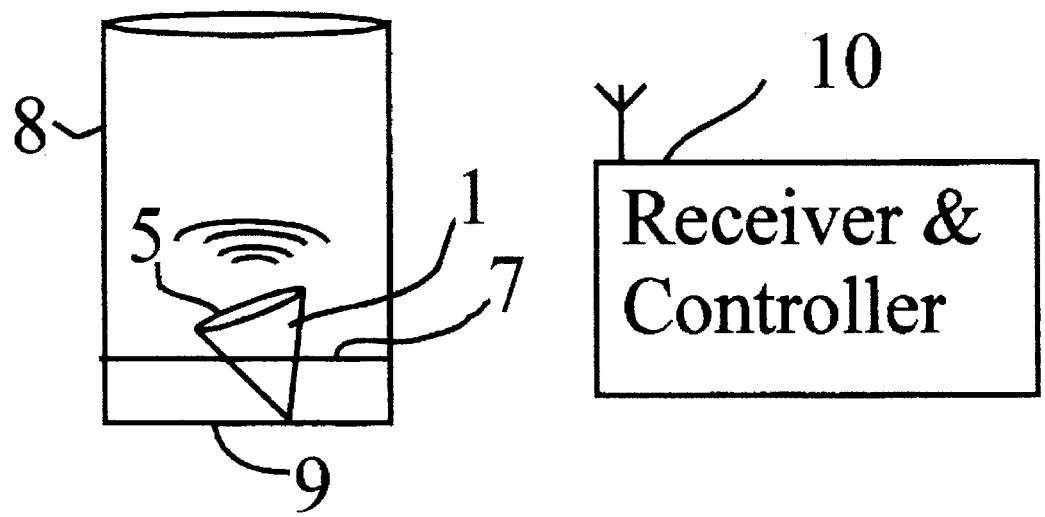
FIGS. 6a and 6b are schematic illustrations of alternative configurations of the device with a receiver and controller unit.
Figure 6B:
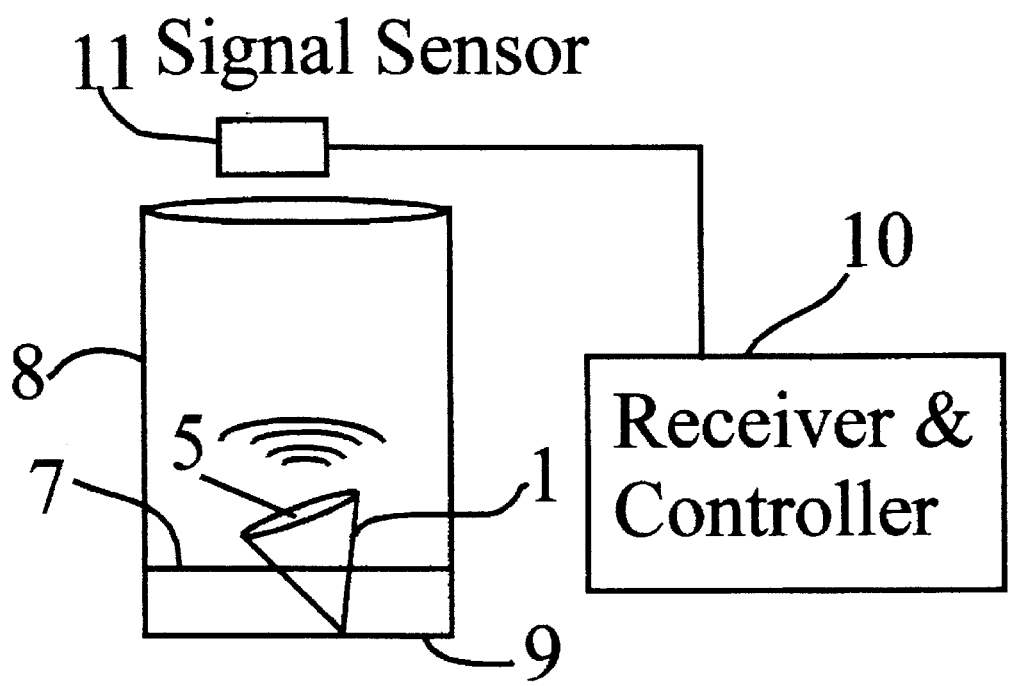

The word "unanchored" refers to that which is not mechanically connected to the container holding the fluid. As shown in FIG. 5a when the separate device (1) floats on the fluid surface (7), it is vertical and the mercury switch will be in the off position, hence there is no current flow. As shown in FIG. 5(b) when the fluid level (7) drops to a point which allows the device (1) to touch the bottom (9) of the container (8), the device will tilt due to its conical shape. As soon as a desired tilt angle (determined by the position of the mercury switch) is achieved, the mercury switch closes the circuit and activates the alarm (for example, light, sound or a frequency, or all together).

The alarm can be designed to simply alert a human operator of the low fluid level, or can be coupled with other devices (for example, through receiver (10) directly or through a sensor (11)) to take remedial action (for example, shutting off a pump or a heat source), or can be coupled to a timer so as to take automatic remedial action if a human operator does not intervene within a predetermined period.

Figure 8:
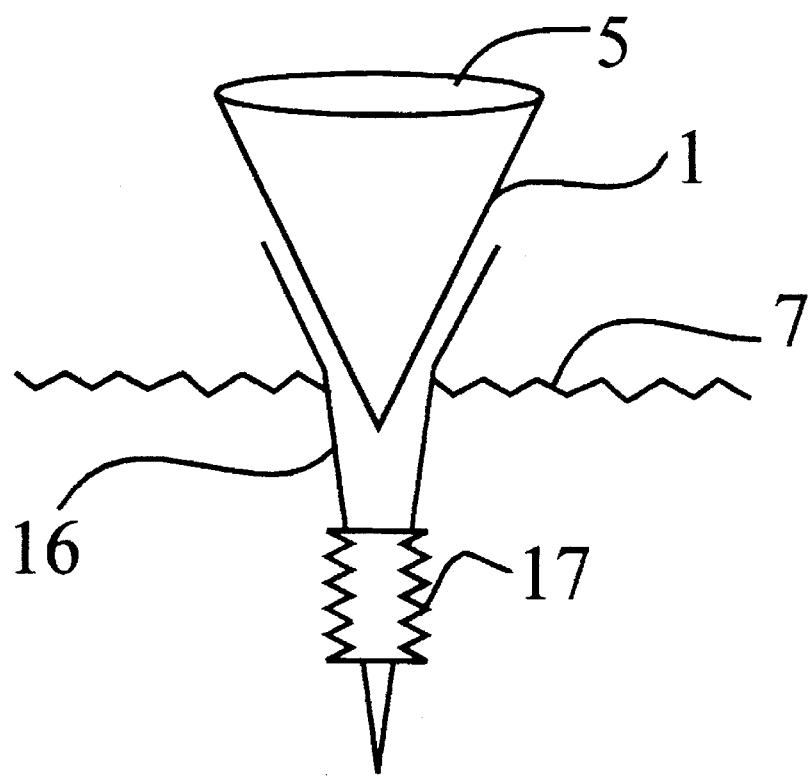
FIG. 8 is a side view of the device attached to a carrier suitable for adjusting the level at which an alarm is triggered.

In addition, as shown in FIG. 8, the device may be attached to a carrier (16) of a suitable size and shape to float when a liquid is above a predetermined level and to contact the container bottom, thus tilt, below said level. The carrier may be made adjustable by screw (17).

The broader usefulness of the invention may be illustrated by the following examples.

EXAMPLE #1

Warning and control of solvent reservoir in Liquid Chromatography:

In column chromatography, a solvent flows through a column and various chemicals and biochemicals are separated in the column. The solvent is applied to the column by means of a pump or hydrostatic pressure to maintain a steady solvent flow through the system. Column chromatography separation needs to be under constant observation, because if the containers with the solvent run empty then the column runs dry. If the column runs without the solvent then it gets dried out due to the air passing through the column. This in turn destroys the column as well as the whole separation process. The column must be replaced and the previously separated substances are lost. Therefore, it is important to monitor the solvent level in the container from time to time and if required to keep refilling the solvent. However, it is most common in the busy daily lab routine and during experiments to sometimes forget refilling. The instant invention provides a device which can be placed in the solvent container without affecting the operation of the separation process and which can either alert the operator when the level is low or can shut off the process.

EXAMPLE #2

Warning of preboiling temperature.

If there is a disturbance of liquid levelness, such as would occur as the liquids approaches boiling, the device will be activated. Therefore, it may be used as passive sensor of imminent boiling.

In addition, an active temperature sensor may be placed in the device (1). The whole unit can be placed in a liquid and the temperature sensor adjusted to 5°–10° below the boiling point. When the preboiling temperature is reached, the device will send a signal warning that boiling is about to occur. This unit can be used in the lab as well as at home for the boiling of fluids, e.g. milk. The signal can be received by a person or a receiver with a built-in controller to take action (e.g. shut off the unit). The same unit can also be used as a wireless remote sensing thermometer or thermostat.

EXAMPLE #3

Remote controlled pH meter.

A pH meter probe (or sensor) can be placed in the device (1). The pH can be measured and the value transmitted to a receiver for control. Such a device would be useful in fermentation or other processes.

EXAMPLE #4

Remote controlled enzyme reactions.

Probes such as biosensors of different types, (for example for oxygen, nitrogen, enzyme, alcohol, glucose, or any other substrate or enzyme reactions) can be included in the device and can be monitored and data can be sent directly to a control unit. More than one biosensor can be used in a single device and each probe can send a digital signal to the receiver and controller for further processing.

EXAMPLE #5

Beverage container empty warning.

The device (1) can be placed in a beverage container since it is inert and easily sterilized. Such a device could either signal that the container was empty or could turn on an "EMPTY" signal on the outside of the container or emit a beeper sound.

As can be seen from the above description, it is possible to implement the invention simply and easily in a variety of applications.

Thus, there has been described a mercury switch encapsulated in a conically shaped inert material sized appropriately to the predetermined fluid limit, and coupled to an alarm device (such as an audible alarm, a radio frequency signal or a light emitting diode). That has a number of novel features, and a manner of making and using the invention.

While a specific embodiment of the invention has been shown and described in detail to illustrate the application of the principles of the invention, it will be understood that the invention may be embodied otherwise without departing from such principles and that various modifications, alternate constructions, and equivalents will occur to those skilled in the art given the benefit of this disclosure. Thus, the invention is not limited to the specific embodiment described herein, but is defined by the appended claims.

What is claimed is:

1. A liquid level sensor device for sensing when liquid in a container has dropped to a predetermined level, comprising a mercury switch affixed to a conical container of a size and density such that said container unanchored floats stably in said liquid until said predetermined level is reached, and tilts so as to close said mercury switch when said liquid drops below said predetermined level.

2. A device as in claim 1 further comprising circuitry for activating an alarm when said mercury switch is closed, but not when said mercury switch is open.

3. A device as in claim 2 wherein said alarm comprises a light source.

4. A device as in claim 2 wherein said alarm comprises a frequency generator.

5. A device as in claim 2 further comprising a receiver for said signals, said receiver being coupled to a control device for controlling the level of said liquid.

6. A device as in claim 2 further comprising a timer for delaying activation of the control device for a predetermined period of time.

7. A device as in claim 1 wherein one side of said cone is weighted so as to insure tilting in a direction which will activate said mercury switch.

8. A liquid level sensor device for sensing when liquid in a container has dropped to a predetermined level, comprising inclinometer means coupled to a switch such that said switch is open when the inclinometer is level and closed when the inclinometer deviates from level by a predetermined amount, said inclinometer and switch being affixed to a conical container floating unanchored in the liquid of such size and density that said container floats stably in said liquid until said predetermined level is reached and tilts so as to cause said inclinometer to close said switch when said liquid drops below said predetermined level.

* * * * *